(12) United States Patent
McCann et al.

(10) Patent No.: US 6,184,392 B1
(45) Date of Patent: Feb. 6, 2001

(54) PROCESS FOR PREPARING 3-ISOCHROMANONE

(75) Inventors: Hannah Sallie Robertson McCann, Stirlingshire; Raymond Vincent Heavon Jones, West Lothian, both of (GB)

(73) Assignee: Zeneca Limited (GB)

( * ) Notice: Under 35 U.S.C. 154(b), the term of this patent shall be extended for 0 days.

(21) Appl. No.: 09/445,491

(22) PCT Filed: May 29, 1998

(86) PCT No.: PCT/GB98/01581

§ 371 Date: Dec. 8, 1999

§ 102(e) Date: Dec. 8, 1999

(87) PCT Pub. No.: WO98/56784

PCT Pub. Date: Dec. 17, 1998

(30) Foreign Application Priority Data

Jun. 11, 1997 (GB) .................................................. 9712166
Aug. 26, 1997 (GB) .................................................. 9718010

(51) Int. Cl.[7] .......................... C07D 311/02; C07D 17/00
(52) U.S. Cl. ........................................... 549/290; 570/101
(58) Field of Search .............................. 549/290; 570/101

(56) References Cited

U.S. PATENT DOCUMENTS

| | | | |
|---|---|---|---|
| 4,424,394 | 1/1984 | Schneider et al. | 560/105 |
| 5,886,211 | 3/1999 | Hirai et al. | 560/105 |

FOREIGN PATENT DOCUMENTS

| | | |
|---|---|---|
| 24 10 782 A1 | 9/1975 | (DE) . |
| 25 26 046 C2 | 1/1976 | (DE) . |

OTHER PUBLICATIONS

Kiji et al., Palladium–Catralyzed, Atmospheric Pressure Carbonylation of Allyic Chlorides in Two–Phase Aqueous Sodium Hydroxide–Organic Solvent Media, Chemistry Letters 957–960 (1988).

Cassar et al., The Use of Phase–Transfer Catalysis in Palladium–Catalyzed Carbonylation of Organic Halides, 121 J. Organomettalic Chem. C55–C56 (1976).

Huang & Wu, Palladium (II)–catalyzed carbonylation of aromatic halides under conditions of phase transfer catalysis, Chemistry & Industry 548 (1990).

Grushin & Alper, Alkali–Induced Disproportionation of Palladium (II) Tertiary Phosphine Complexes, $[L_2PdCl_2]$, LO and Palladium (0). Key Intermediates in the Biphasic Carbonylation of ArX Catalyzed by $L_2PdCl_2$, 12 Organometallics 1890–1901 (1993).

Ito et al., Effect of Base Palladium–Black Catalyzed Carbonylation of Iodobenzene, 48 (7) Bull. Chem. Soc. Japan 2091–2094 (1975).

Bergbreiter et al., New strategies in using macromolecular catalysts in organic synthesis, 74 J. Molecular Catalysis 409–419 (1992).

Kohlpaintner & Beller, Palladium–catalyzed carbonylation of benzyl chlorides to phenylacetic acids—a new two–phase process, 116 J. Molecular Catalysis A: Chem. 259–267 (1997).

Cowell & Stille, Synthesis of Lactones by the Palladium–Catalyzed Carbonylation of Halo Alcohols, 102 (12) J. American Chem. Soc. 4193–4198 (1980).

Sim et al., Palladium (O) Complex Catalyzed Mono–Carbonylation of Xylylene Dihalides under Phase Transfer Agent (II), 9 (3) Bull. Korean Chem. Soc. 185–187 (1988).

Shanyan et al., Catalysis of Heteronuclear Metal Cluster III. Hydroformylation of 2–Butene, 1 (2) J. Molecular Catalysis 115–119 (Jun. 1987).

*Primary Examiner*—Charanjit S. Aulakh
(74) *Attorney, Agent, or Firm*—Thomas R. Savitsky

(57) ABSTRACT

3-Isochromanome is prepared by reacting an o-xylene-$\alpha,\alpha'$-dihalide with carbon monoxide and water in the presence of a metal catalyst such that the pH of the reaction is maintained between about 7 and 11.

10 Claims, No Drawings

PROCESS FOR PREPARING 3-ISOCHROMANONE

This application is a 371 of PCT/GB98/01581 filed May 29, 1998, now WO 98/56784 Dec. 17, 1998.

This invention relates to a chemical process and more particularly to a process for preparing 3-isochromanone which is useful in the manufacture of certain agricultural products.

3-Isochromanone is a well known compound and a number of methods for its preparation are described in the chemical literature. In particular, a process is described in WO97/00850 which comprises reacting an o-xylene-α,α'-dihalide derivative with carbon monoxide and water in an organic solvent in the presence of a catalyst and a hydrogen halide capturing agent followed by treatment with an acid. It has now been found that the final acid treatment can be obviated by careful control of the pH during reaction, thereby providing a simpler process.

Thus, according to the present invention, there is provided a process for the preparation of 3-isochromanone which comprises reacting an o-xylene-α,α'-dihalide with carbon monoxide and water in the presence of a catalyst, characterised in that the pH of the reaction is maintained between 7 and 11.

The o-xylene-α,α'-dihalide starting material has the general formula:

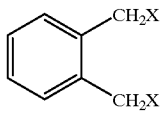

where X is a halogen atom such as chlorine, bromine or iodine, especially chlorine or bromine. o-Xylene-α,α'-dichloride is a particularly convenient starting material.

The pH of the reaction is maintained by having present at the beginning a sufficient amount of a suitable base, or by the controlled addition during the reaction of a suitable base at a suitable rate, or by buffering. Alternatively, it may be maintained by a combination of these methods. Suitable bases include inorganic bases such as alkali metal or alkaline earth metal carbonates, bicarbonates or hydroxides, for example, sodium or magnesium carbonate, potassium or sodium bicarbonate or calcium or magnesium hydroxide, or organic bases such as carboxylate salts, for example acetate salts. Quantities and rates of addition of the base should be sufficient to maintain the pH in the range of 7 to 11, suitably 7 to 10, for example, 8 to 10.

Conveniently the process is carried out in an organic solvent which is inert to the reactants. Any suitable organic solvent may be used, either water soluble or water immiscible. Examples are saturated or aromatic hydrocarbons or halogenated derivatives thereof, such as chlorinated or fluorinated derivatives, for example methylene chloride, toluene or chloro- or fluorobenzene, polar aprotic solvents such as N,N-dimethylformamide, ethers such as cyclic ethers, for example tetrahydrofuran, aliphatic ethers, for example dialkyl ethers, aromatic ethers, for example phenyl alkyl ethers and polyethers such as polyethylene glycols and variants thereof, for example, end-capped polyether glycols, alcohols such as t-butanol, nitrites, amines, ketones and esters. The choice of solvent may be influenced by the use to which the 3-isochromanone will be put. Of particular interest are $C_{1-6}$ and especially $C_{1-4}$ dialkyl ethers like methyl t-butyl ether and methyl t-amyl ether. It is envisaged, however, that the reaction may be carried out in water with no solvent present. One example of this is to carry out the process at a temperature above the melting point of the o-xylene-α,α'-dihalide, which, in the case of o-xylene-α,α'-dichloride is about 55° C. As 3-isochromanone melts at 82 to 84° C., a reaction temperature below this may be of advantage in allowing 3-isochromanone to crystallise out and allowing isolation of 3-isochromanone by filtration or extraction in a suitable solvent.

The total water requirement may be introduced at the start of reaction, added continuously or stepwise during reaction or formed in situ.

The carbon monoxide will normally be added by feeding a continuous supply of the gas into the reaction mixture either at atmospheric pressure or at pressures up to 100 atmospheres, for example at from 1 to 5 atmospheres. The pressure chosen will depend on the equipment in which the reaction is carried out and the required reaction rates and yield.

Any suitable carbonylation catalyst may be used in the process of the invention, particularly Group VIII (first, second and third triads) metal catalysts, for example palladium, cobalt or iron catalysts. Especially suitable are palladium catalysts, for example palladium (0) and palladium (II) catalysts, which may be water-soluble or water-insoluble, supported on a carrier, such as carbon, silica, calcium carbonate, a clay such as Montmorillonite, a polymer or other inert solid, or unsupported. Supported catalysts have the advantage of facilitating catalyst recovery and recycling. Ligands such as triphenylphosphine may be used in conjunction with certain palladium catalysts or it may be beneficial to pre-reduce the catalyst with hydrogen, or another suitable reducing agent.

Suitable water-soluble palladium catalysts in the form of phoshine complexes are described, for example, by J. Kiji et al in *Chem. Lett.*, 957–960 (1988). Suitable water-insoluble palladium catalysts include bis(triphenylphosphine) palladium dichloride and tetrakis(triphenylphosphine) palladium (0) which are described by L. Cassar et al in *J. Organometallic Chem.*, 121 (1976), C55-56, in DE-A-2526046 and by X. Huang et al in *Chem. & Ind., Sep. 3*, 1990, 548. Palladium (II) catalysed carbonylation reactions are also discussed by V. Grushin et al in *Organometallics*, 12 (5), 1890-1901 (1993). The use of a supported carbonylation catalyst in the form of palladium-black is described by T. Ito et al in *Bull. Chem. Soc. Japan*, 48 (7), 2091–2094 (1975). The use of soluble triphenylphosphine ligands to activate palladium catalysts is described by D. Bergbreiter et al in *J. Mol. Catalysis*, 74 (1992), 409–419. Other suitable catalysts and ligands, including water soluble ones, are described in WO 97/00850. The ligands may be used in amounts up to 20 mole equivalents of palladium, and suitably in the range of from 0.5 to 5.0 mole equivalents of palladium. The amount of palladium catalyst used may be in the range of 0.000001 to 0.5 mole equivalents of the o-xylene-α,α'-dihalide.

When the process is carried out in a two-phase system, for example when a water-immiscible solvent is used, it may be advantageous to include a phase transfer catalyst. By the term "phase transfer catalyst" is meant a substance which, being at least partly present in or wetted by a first (usually organic) phase, promotes reaction between a reactant in the first phase and a reactant which it transfers to the first phase from a second (usually aqueous but sometimes solid) phase. After reaction, the phase transfer catalyst is released for transferring further reactant. Phase transfer catalysts are reviewed by E. V. Dehmlow in *Angewante Chemie* (International Edition), 13 (3), 170 (1974). Other reviews are by Jozef Dockx in *Synthesis* (1973), 441–456 and by C. M. Starks in JACS., (93) 1, Jan. 13, 1971, 195–199.

Suitably the phase transfer catalyst is a quaternary ammonium or phosphonium salt preferably containing bulky organic groups, usually alkyl or aralkyl groups, to make it soluble in the organic phase. It is preferred that the phase catalyst is a tetraalkyl or aralkyl (eg benzyl) trialkyl ammonium or phosphonium salt in which the total number of carbon atoms attached to each nitrogen or phosphorus atom is greater than 10. There is little advantage in the number being above 70. It is especially preferred that the number should be in the range of from 16 to 40.

Examples of quaternary ammonium salts are: cetyltrimethylammonium bromide, dicetyldimethylammonium chloride, octyltributylammonium bromide, trioctylmethylammonium chloride (available as Aliquat™ 336), benzyldimethyllaurylammonium chloride, benzyltriethylammonium chloride, dilauryldimethylammonium chloride, tetrabutylammonium bromide and dieicosyldimethylammonium chloride. Examples of quaternary phosphonium salts are cetyltripropylphosphonium bromide and triphenylethylphosphonium bromide. Other phase transfer catalysts which may be suitable include crown ethers and polyethylene glycol variants. If used, the phase transfer catalyst may be present in an amount ranging from 0.001 to 0.5 mole equivalents of the o-xylene-α,α'-dihalide.

The process may be carried out at any suitable temperature within a range of from −20° C. to 180° C., for example from 10° C. to 130° C., typically from ambient temperature to 110° C. .

In one aspect of the process, when using a water-immiscible organic solvent and a palladium catalyst which is soluble in the organic layer, the 3-isochromanone and catalyst are found in the organic layer and inorganic by-products in the aqueous layer. The latter is then discarded and the 3-isochromanone extracted from the organic layer by the addition of aqueous base to form a salt of the corresponding hydroxy acid. This aqueous layer is separated and the 3-isochromanone regenerated by suitable pH adjustment. The organic layer retains the palladium catalyst for recycling and reuse.

In another aspect of the process, when using a water-immiscible organic solvent and a palladium catalyst which is soluble in the aqueous layer, the 3-isochromanone is found in the organic layer and the palladium catalyst in the water layer. The organic layer is separated for isolation of the 3-isochromanone. The remaining aqueous layer is acidified and the palladium catalyst extracted into an organic solvent. The aqueous layer is then discarded. The palladium catalyst is recovered for recycling and reuse by extraction of the organic layer with aqueous base. A two-phase carbonylation process of this type using a water-soluble palladium catalyst is described by C Kohlpaintner in *J. Mol. Catalysis A. Chem.* 116 (1997)

The use of a supported palladium catalyst has the advantage that it can be filtered from any reaction mixture using known technology, thereby facilitating its recycling and reuse.

3-Isochromanone is useful, inter alia, as an intermediate in the manufacture of agricultural products, especially fungicides of the strobilurin type, for example, those described in EP-A-278595.

The invention is illustrated by the following Examples in which:

g = grammes
ml = milliliters
mol = moles
eq = equivalents
mmol = micromoles
mol % = moles expressed as a percentage of moles of starting material
M = molar
° C. = degrees centigrade
gc = gas chromatography
mp = melting point

EXAMPLE 1

Dichloromethane (20 ml), potassium bicarbonate (30 ml, 2M) and benzyltriethylammonium chloride (0.2 eq) were charged to a 100 ml round bottom flask at room temperature. Carbon monoxide was slowly bubbled through for 30 minutes then tetrakis (triphenylphosphine) palladium (0) (0.29 g, 8 mol %) dissolved in dichloromethane was charged using a syringe. After 1 hour the o-xylene-α,α'-dichloride (0.53 g, 1 eq), dissolved in dichloromethane, was charged using a syringe. Carbon monoxide was slowly and continuously bubbled through the reaction overnight. The pH of the aqueous layer was 9.4. The reaction mixture was worked up by separating off the organic layer and washing with water (2×10 ml). Qualitative gc analysis showed 55% starting material, 15% 3-isochromanone and 29% triphenylphosphine.

EXAMPLE 2

The procedure of Example 1 was repeated except that no benzyltriethylammonium chloride phase transfer catalyst was used. The pH of the final reaction mixture aqueous layer was 9.6. Qualitative gc analysis of the organic layer showed 20% starting material, 16% 3-isochromanone and 43.7% triphenylphosphine.

EXAMPLE 3 o-Xylene-α,α'-dichloride (2.2 g, 1 eq), potassium bicarbonate (2M, 30 ml, 20 eq) benzyltriethylammonium chloride (0.149 g, 0.2 eq) were charged to a 100 ml round bottom flask and heated to 80° C. while bubbling through carbon monoxide. The o-xvlene-α,α'-dichloride melted and after 15 minutes tetrakis (triphenylphosphine) palladium (0) (0.29 g, 8 mol %) was charged. The reaction mixture was heldat 80° C. for 4 hours then cooled to room temperature and held overnight with stirring and with carbon monoxide bubbling through. The pH of the aqueous layer at the end of reaction 8–9 (pH papers). Testing by qualitative gc analysis of the organic phase contained 26% starting material and 28% 3-isochromanone.

EXAMPLE 4

Toluene (36 g), triphenylphosphine (2.1 g, 0.4 eq), Aliquat™ 336 (1.3 g, 0.16 eq), potassium bicarbonate (8.48 g, 4.2 eq) and o-xylene-α,α'-dichloride (3.5 g, 1 eq) were charged to a 100 ml round bottom flask and heated to 75° C. while bubbling carbon monoxide slowly through the reaction mixture. Palladium/carbon (2%, 2.12 g, 0.02 eq) was charged with water (10 ml) under a carbon monoxide atmosphere. The reaction was held at 75° C. with carbon monoxide bubbling through slowly overnight. The reaction mixture was filtered to remove the palladium/carbon solids. The pH of the aqueous layer was 10.8. The filtrates were separated and the organic layer was washed with water. The organic layer showed 9% 3-isochromanone and 2.4% starting material by qualitative gc.

EXAMPLE 5

The procedure of Example 4 was repeated except that 0.212 g 2% palladium/carbon (0.002 eq) and 0.21 g triphenylphosphine (0.04 eq) were used. Qualitative gc analysis after 30 hours at 75° C. showed 0.1% starting material and 35% 3-isochromanone in the organic layer. The pH of the final aqueous layer was 9.

EXAMPLE 6

The procedure of Example 4 was repeated except that 5% Palladium on calcium carbonate (0.85 g, 0.02 eq) and triphenylphosphine (2.1 g, 0.4 eq) were used. Qualitative g.c. analysis after 6 hours at 70° C. showed 25% starting material and 35% 3-isochromanone. Qualitative gc analysis after 22 hours showed 2% starting material and 63% 3-isochromanone, in the organic layer. The pH of the final aqueous layer was 9.

EXAMPLE 7 o-Xylene-α,α'-dichloride (7 g, 0.04mol), potassium bicarbonate (16.97 g, 0.168 mol), triphenylphosphine (0.1177 g, 0.00044 mol) N,N-dimethylformamide (58.5 g, 0.8 mol) and water (7.2 g, 0.4 mol) were charged to a 100 ml round bottom flask. Carbon monoxide was bubbled through with agitation and the reaction mixture heated to 70° C. At this temperature dichlorobis(triphenylphosphine)palladium (II) (0.1418 g, 0.0002 mol) in N,N-dimethylformamide (10 ml) was injected into the flask in 0.5 ml aliquots over 3 hours. A sample was withdrawn half-way through the catalyst addition for qualitative gc analysis This showed 5% 3-isochromanone. Stirring and carbon monoxide addition was continued overnight and the reaction mixture was sampled again for qualitative gc analysis. This showed no starting material and 61% isochromanone. The reaction mixture was filtered and the solvent in the organic layer from the filtrates was removed by vacuum. The resulting oil was extracted into toluene (60 ml) and water (60 ml). The layers were separated and the organic layer had solvent removed by vacuum. The resulting amber oil was extracted into dichloromethane (25 ml) and washed with water (2×25 ml). Dichloromethane was removed by vacuum. 3-Isochromanone was then crystallised from the resulting oil. This was analysed quantitatively by gc, giving an isolated yield of 17.7%.

EXAMPLE 8 o-Xylene-α,α'-dichloride (7.07 g), 1.0 eq, 0.04 mol) was charged to a flask, followed by toluene (85 ml), potassium bicarbonate (16.97 g, 4.2 eq) and Aliquat™ 336 (1.62 g, 0.1 eq). The stirred mixture was heated to 70° C. and purged with a stream of carbon monoxide gas for 30 minutes. A suspension of dichlorobis(triphenylphosphine) palladium (II) (284 mg, 1 mol %) and triphenylphosphine (233 mg, 2.2 mol %) in toluene (5 ml) was prepared and 1 ml portions of this were added to the reaction mixture every 20 minutes. The mixture was heated at 70° C. under a stream of carbon monoxide for 17½ hours, then cooled to ambient temperature. Deionized water (50 ml) was added and the organic phase collected and concentrated in vacuo. The black residue was recrystallised from toluene/methylcyclohexane to give a grey solid. Quantitative analysis of the solid (4.07 g, 71.1% strength) and the mother liquors (8.99 g, 13% strength) indicated a 68% yield of 3-isochromanone.

EXAMPLE 9 o-Xylene α,α'-dichloride (3.5 g, 1 eq), palladium/carbon filtered from Example 5 (0.28 g), triphenylphosphine (0.21 g, 0.04 eq), potassium bicarbonate (8.48 g, 4.2 eq), Aliquat™ 336 (1.3 g, 0.16 eq), toluene (36 g) and water (10 ml) were charged to a 100 ml round bottom flask and sparged with carbon monoxide. The temperature was raised to 70° C. and held with fast agitation while carbon monoxide was bubbled slowly through the reaction mixture. Qualitative gc analysis after 5 hours showed 27.5% starting material and 1% 3-isochromanone in the organic layer. After holding overnight with carbon monoxide bubbling through at 70° C., qualitative gc analysis showed 11% starting material and 11% 3-isochromanone in the organic layer. The pH of the final reaction mixture aqueous layer was 10.4.

EXAMPLE 10 o-Xylene α,α'-dichloride (3.5 g, 1 eq), dichlorobis (triphenylphosphine) palladium (II) (0.1418 g, 0.01 eq), triphenylphosphine (0.1165 g, 0.022 eq), potassium bicarbonate (8.48 g, 4.2 eq) and polyethylene glycol 400 (40 g, 5 eq) were charged to a 100 ml round bottom flask and carbon monoxide bubbled through whilst heating the reaction to 70° C. After stirring at 70° C. overnight qualitative gc analysis showed no starting material and 9% 3-isochromanone by area %.

EXAMPLE 11 o-Xylene α,α'-dichloride (3.5 g, 1 eq), dichlorobis (triphenylphosphine) palladium (II) (0.1418 g 0.01 eq), triphenylphosphine (0.1165 g, 0.022 eq), potassium bicarbonate (8.48 g, 4.2 eq), Aliquat™ 336 (0.808 g, 0.1 eq) and t-amylmethylether (43.4 g) were charged to a 100 ml round bottom flask and carbon monoxide bubbled through whilst heating the reaction mixture to 70° C. After stirring at 70° C. overnight qualitative gc analysis showed 0.1% starting material and 58.4% 3-isochromanone by area %.

EXAMPLE 12 o-Xylene α,α'-dichloride (5.0 g, 29 mmol), potassium bicarbonate (12.1 g, 121 mmol), Aliquat™ 336 (1.2 g, 3 mmol), palladium on Montmorillonite catalyst (0.0641 g, ~0.011 mmol) and toluene (52.90 g, 574 mmol—prepared as described below) were charged to a 100 ml three-necked round bottomed flask with stirring (650 rpm). A steady flow of carbon monoxide was bubbled through the reaction mixture whilst heating to 70° C. Triphenylphosphine (180.0 mg, 0.69 mmol) was dissolved in approximately 3 ml of toluene, and once the reaction mixture had reached temperature, this solution was charged by syringe in suitable aliquots, over a 30 minute period. After a further 1.5 hours, the reaction mixture was sampled for qualitative gas chromatographic analysis which showed that there had been no significant conversion to the desired product. A further charge of palladium on Montmorillonite catalyst (1.64 g, 0.3 mmol) was added to the reaction mixture in one portion. The reaction mixture was maintained at 70° C., with carbon monoxide bubbling through and vigorously stirred for an additional 16 hours, before sampling for qualitative gas chromatographic analysis. Results showed the ratio of 3-isochromanone to starting material to be >99:1 by area percent. The reaction mixture was cooled to ambient temperature and the carbon monoxide supply was stopped.

The slurry was filtered through a GF/B Whatman filter (#3) and the clear amber toluene solution (46.78 g) analysed for isochromanone content. The remaining cake was washed with toluene (2×10 ml), and the washings (16.64 g) retained for analysis. The total quantitative yield of 3-isochromanone by gc analysis (including washings) was 57.9%. After further washing with water (20 ml) and hexane (20 ml) the black solid (recovered palladium on Montmorillonite catalyst) was dried by suction and reused in Example 13.

Preparation of Palladium on Montmorillonite Catalyst

Montmorillonite K10 (10.0 g) was slurried in saturated sodium chloride (57.0 g) for 18 hours at room temperature and filtered to give a wet grey solid. The solid was washed with water (10 ml) and dried by suction. It was then slurried in 0.1 M hydrochloric acid (~50 ml) for 24 hours, filtered by suction, washed with water until the washings were pH neutral, and dried by suction. The washed solid was slurried in toluene (70 ml) and 20 ml removed by azeotropic distillation in order to dry the slurry. 2-Diphenylphosphinoethyltriethoxysilane (1.13 g, 0.003mol) was added in one portion and the reaction mixture heated at reflux for 48 hours, before cooling to ambient temperature and filtering by suction. The solids were washed with toluene (3×50 ml) to remove all unreacted silane, and dried by suction. They were then slurried in toluene (50 ml), and dichlorobis(benzonitrile) palladium (II) (1.20 g, 0.003 mol) was added in one portion. The slurry was stirred at room temperature for 24 hours, before filtering off an orange powder, which was washed with toluene (3×50 ml) and dried by suction. Approximately 8 g of solid was recovered.

EXAMPLE 13 o-Xylene α,α'-dichloride (5.0 g, 29 mmol), potassium bicarbonate (12.1 g, 121 mmol), Aliquat™ 336 (1.2 g, 3 mmol), recycled catalyst (from Example 12) and toluene (52.9 g, 574 mmol) were charged to a 100 ml three-necked round bottomed flask with stirring. A steady flow of carbon monoxide was bubbled through the reaction mixture whilst heating to 70° C. Triphenylphosphine (180.9 mg, 0.69 mmol) was dissolved in approximately 3 ml of toluene, and once the reaction mixture had reached temperature, this solution was charged by syringe in suitable aliquots, over a 30 minute period. The reaction mixture was maintained at 70° C. with carbon monoxide bubbling through and vigorously stirred for an additional 15 hours, before sampling for qualitative gas chromatographic analysis. Results showed the ratio of 3-isochromanone to starting material to be >99:1 by area percent. The reaction mixture was cooled to ambient temperature and the carbon monoxide supply was stopped. The slurry was filtered through a GF/B Whatman filter (#3) and the clear amber toluene solution (39.62 g) analysed for isochromanone content. The remaining cake was washed with toluene (2×10 ml), and the washings (15.5 g) retained for analysis. The total quantitative yield of 3-isochromanone by gc analysis (including washings) was 49.0%. After further washing with water (20 ml) and hexane (20 ml) the black solid (recovered palladium onn Montmorillonite catalyst) was dried by suction and reused in Example 14.

EXAMPLE 14 o-Xylene α,α'-dichloride (5.0 g, 29 mmol), potassium bicarbonate (12.1 g, 121 mmol), Aliquat™ 336 (1.2 g, 3 mmol), recycled catalyst (from Example 13) and toluene (52.9 g, 574 mmol) were charged to a 100 ml three-necked round bottomed flask with stirring. A steady flow of carbon monoxide was bubbled through the reaction mixture whilst heating to 70° C. Triphenylphosphine (186.5 mg, 0.7 mmol) was dissolved in approximately 3 ml of toluene, and once the reaction mixture had reached temperature, this solution was charged by syringe in suitable aliquots, over a 30 minute period. The reaction mixture was maintained at 70° C., with carbon monoxide bubbling through and vigorously stirred for 13 hours, before sampling for qualitative gas chromatographic analysis. Results showed the ratio of 3-isochromanone to starting material to be 87:13 by area percent. After a further 3 hours under the reaction conditions, the qualitative gas chromatographic analysis showed the ratio of 3-isochromanone to starting material to be 95:5 by area percent. After an additional 4 hours under the reaction conditions, the qualitative gas chromatographic analysis showed the ratio of 3-isochromanone to starting material to be >99:1. The reaction mixture was cooled to ambient temperature and the carbon monoxide supply was stopped. The slurry was filtered through a GF/B Whatman filter (#3) and the clear amber toluene solution (25.69 g) analysed for isochromanone content. The remaining cake was washed with toluene (2×10 ml), and the washings (16.28 g) retained for analysis. The total quantitive yield of 3-isochromanone by gc analysis (including washings) was 54.8%. After further washing with water (20 ml) and hexane (20 ml) the black solid (recovered palladium on Montmorillonite catalyst) was dried by suction.

COMPARATIVE EXAMPLE 15

This Example forms no part of the present invention and is included for comparative purposes only. It illustrates that when the pH of the carbonylation reaction mixture is allowed to rise to 12, no 3-isochromanone is formed without an acidification step.

Toluene (25 ml), dichlorobis(triphenylphosphine) palladium (II), (0.1 g, 1.1 mol. %), triphenylphosphine (0.075 g, 2.3 mol %) and o-xylene-α,α'-dichloride (2.2 g. 1 eq) were charged to a 100 ml round bottomed flask which was degassed and filled 4 times with carbon monoxide. The temperature was raised to 70° C. and potassium hydroxide as a 1.8% solution was added to maintain the pH of the reaction between 9 and 9.5. The pH steadied out at around 12 after approx. 0.15 eq of potassium hydroxide solution was charged. Qualitative gc analysis showed 93% starting material and no 3-isochromanone in the organic layer. The acidified aqueous layer showed 19.2% starting material and 6% 3-isochromanone.

What is claimed is:

1. A process for the preparation of 3-isochromanone which comprises reacting an o-xylene-α,α'-dihalide with carbon monoxide and water in the presence of a metal catalyst, wherein the pH of the reaction is maintained between about 7 and about 11.

2. A process according to claim 1 in which the o-xylene-α,α'-dihalide is o-xylene-α,α'-dichloride.

3. A process according to claim 1 in which the pH of the reaction is maintained between 7 and 10.

4. A process according to claim 1 in which the pH of the reaction is maintained between 8 and 10.

5. A process according to claim 1 which is carried out in the presence of an inert organic solvent.

6. A process according to claim 1 in which the reaction is carried out at about atmospheric pressure or at a pressure up to about 100 atmospheres.

7. A process according to claim 1 in which the catalyst is a palladium catalyst.

8. A process according to claim 1 in which the catalyst is present in the amount of about 0.000001 to about 0.5 mole equivalents of the o-xylene-α,α'-dihalide.

9. A process according to claim 1 in which there is present a phase transfer catalyst.

10. A process according to claim 1 which is carried out at a temperature of from about −20° C. to about 180° C.

* * * * *